(12) United States Patent
Campbell et al.

(10) Patent No.: US 6,984,242 B2
(45) Date of Patent: Jan. 10, 2006

(54) IMPLANTABLE MEDICAL DEVICE ASSEMBLY

(75) Inventors: Carey V. Campbell, Flagstaff, AZ (US); William H. Wiley, Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

(21) Appl. No.: 10/325,200

(22) Filed: Dec. 20, 2002

(65) Prior Publication Data

US 2004/0122503 A1    Jun. 24, 2004

(51) Int. Cl.
    *A61F 2/06*      (2006.01)
(52) U.S. Cl. .................. 623/1.12; 623/1.23
(58) Field of Classification Search ............. 623/1.11, 623/1.12, 1.23, 2.11
    See application file for complete search history.

(56) References Cited

U.S. PATENT DOCUMENTS

| | | | | |
|---|---|---|---|---|
| 3,527,650 A | * | 9/1970 | Block ........................ 87/1 |
| 5,296,292 A | | 3/1994 | Butters ...................... 428/375 |
| 5,476,589 A | | 12/1995 | Bacino .................. 210/500.36 |
| 5,801,319 A | | 9/1998 | Hebestreit et al. ............. 84/297 |
| 5,873,906 A | | 2/1999 | Lau et al. ..................... 623/1 |
| 5,883,319 A | | 3/1999 | Hebestreit et al. ............. 84/297 |
| 5,907,113 A | | 5/1999 | Hebestreit et al. ............. 84/297 |
| 5,919,225 A | | 7/1999 | Lau et al. ..................... 623/1 |
| 5,961,440 A | | 10/1999 | Schweich, Jr. et al. ....... 600/16 |
| 6,015,429 A | | 1/2000 | Lau et al. ..................... 623/1 |
| 6,045,497 A | | 4/2000 | Schweich, Jr. et al. ....... 600/16 |
| 6,050,936 A | | 4/2000 | Schweich, Jr. et al. ....... 600/16 |
| 6,248,942 B1 | | 6/2001 | Hebestreit et al. ............. 84/297 |
| 6,261,222 B1 | | 7/2001 | Schweich, Jr. et al. ....... 600/16 |
| 6,302,891 B1 | * | 10/2001 | Nadal ......................... 606/108 |
| 6,315,792 B1 | * | 11/2001 | Armstrong et al. ........ 623/1.23 |
| 6,352,561 B1 | | 3/2002 | Leopold et al. ............. 623/123 |
| RE38,091 E | * | 4/2003 | Strecker .................... 623/1.12 |
| 6,616,684 B1 | * | 9/2003 | Vidlund et al. ............. 606/213 |
| 6,673,105 B1 | * | 1/2004 | Chen ......................... 623/1.15 |

* cited by examiner

*Primary Examiner*—Corrine McDermott
*Assistant Examiner*—Thomas Sweet
(74) *Attorney, Agent, or Firm*—Eric J. Sheets

(57) ABSTRACT

The present invention is directed to implantable medical device assemblies. The assemblies are primarily used to introduce and deposit implantable medical devices in the vasculatures of implant recipients. The principle implantable medical device used in the assembly is an expandable element in the form of an endovascular device. The expandable element is maintained in a compacted configuration during introduction of the device into the vasculature with a confinement means. The expandable element is released from the confinement means at an implantation site with a control line. The control line has high tensile strength, high modulus, structural rigidity, and low compressibility. These features of the control line provide a practitioner with tactile feedback of the release of the expandable element from the confinement means. The tactile feedback is present during the entire deployment of the expandable element. The tactile feedback enables the practitioner to better track and control deployment of the expandable element at an implantation site.

13 Claims, 13 Drawing Sheets

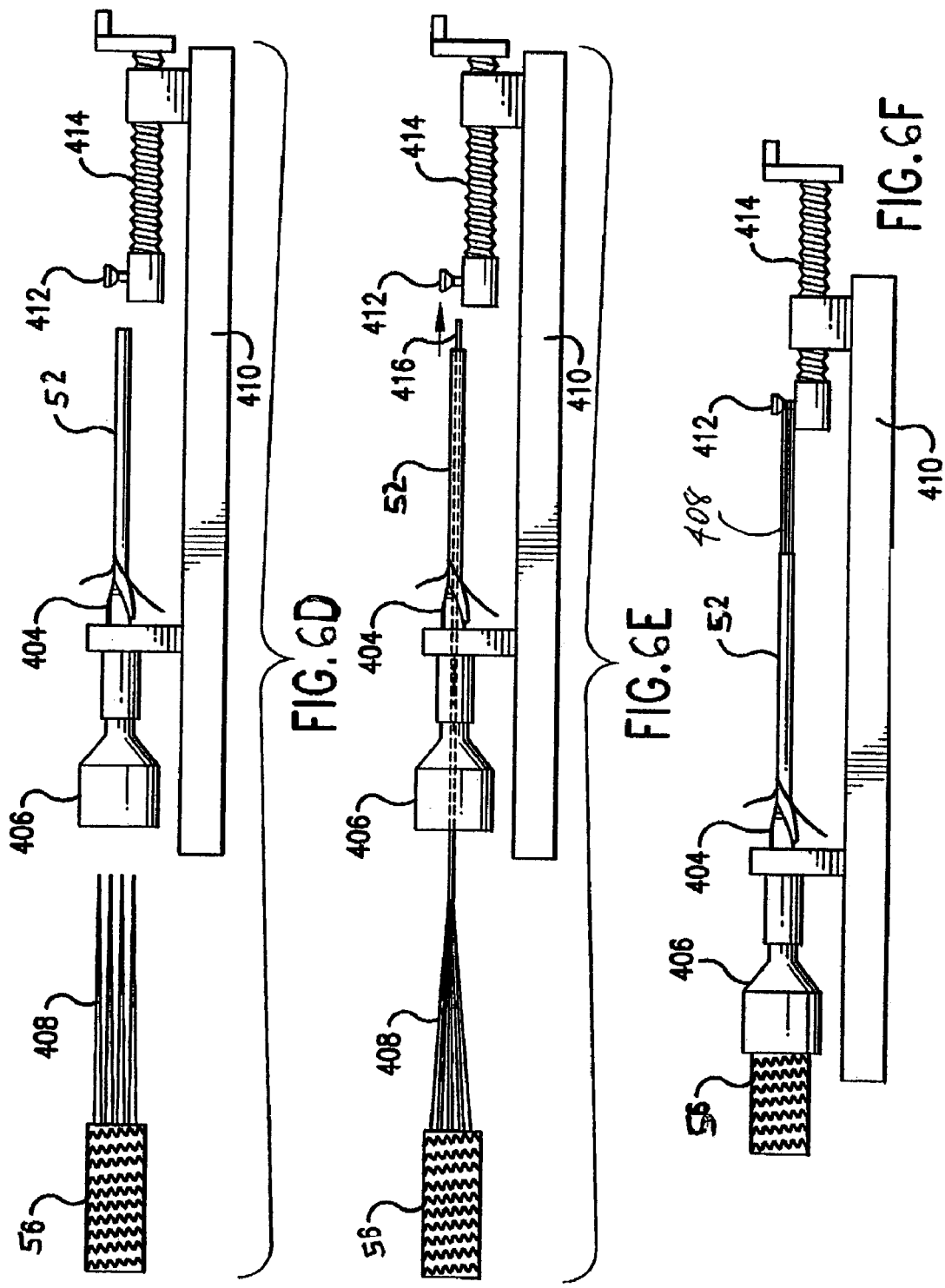

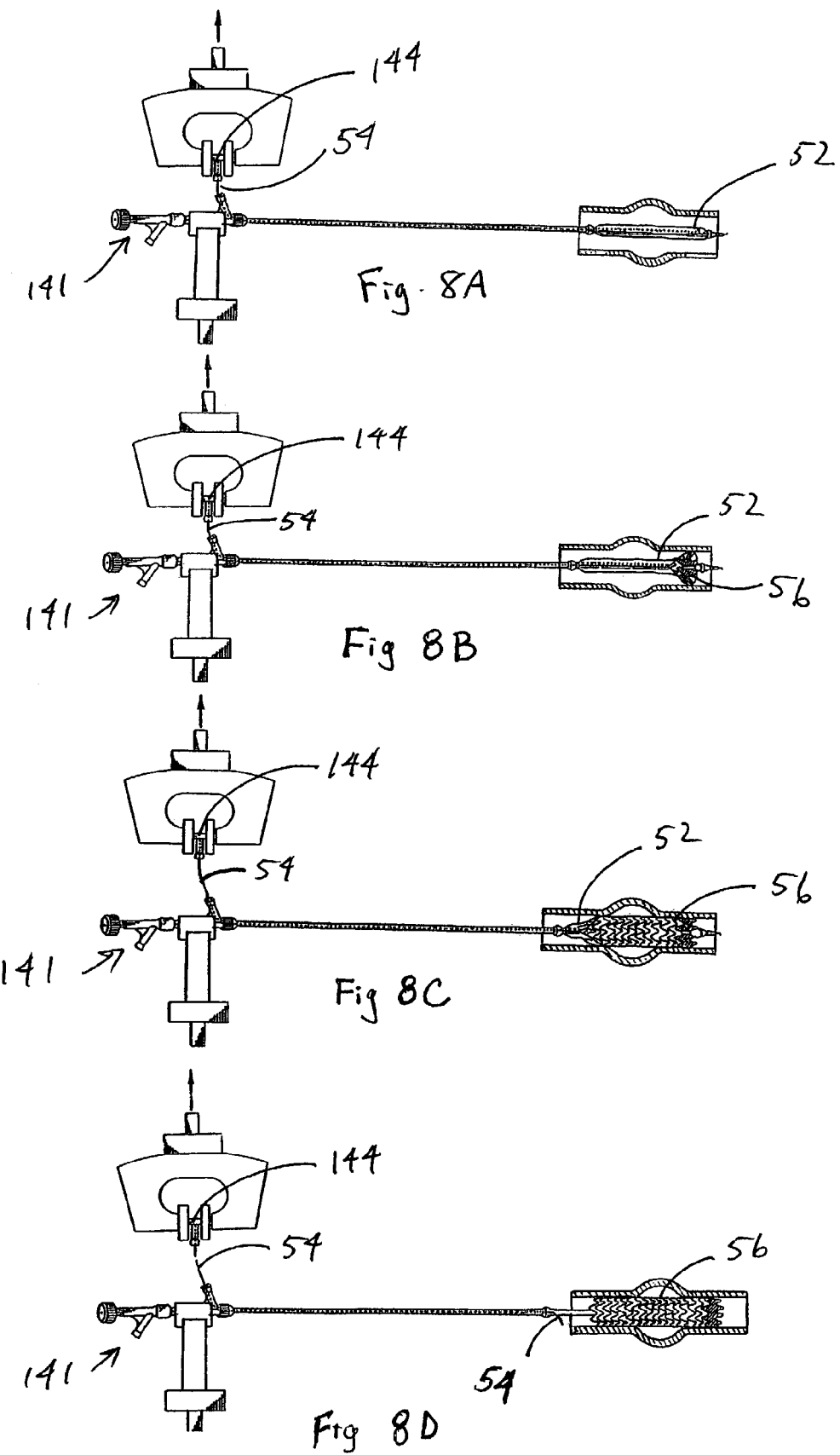

IMPLANTABLE MEDICAL DEVICE ASSEMBLY

FIELD OF THE INVENTION

The present invention relates generally to medical devices. In particular, the invention is directed to implantable medical device assemblies for intravascular introduction and deployment of expandable medical prostheses at an implantation site.

BACKGROUND OF THE INVENTION

Various implantable medical devices for repairing or reinforcing cardiac and vascular structures have been developed in recent years. Some of these devices can be implanted inside a particular vascular structure through so-called interventional, or endovascular, techniques. Interventional techniques involve surgically accessing the vascular system through a conveniently located artery or vein and introducing distal portions of a medical device assembly into the vascular system through the arterial or venous access point. Once the medical device assembly is introduced into the vascular system, it is threaded through the vasculature to an implantation site while proximal portions of the assembly having manually operated control means remain outside the body of the implant recipient. The medical device component of the assembly is then deposited at the implantation site and the remainder of the distal portion of the medical device assembly removed from the vascular system through the access point.

Exemplary interventional medical device assemblies include a catheter. The catheter can be used to precisely position the medical device at an implantation site as well as participate in deployment of the medical device at the implantation site. Some catheters have guidewires running their length to aid in positioning and deployment of the medical device. As an alternative to the guidewire, a catheter can have a moveable inner sleeve running inside the length of the catheter. The inner sleeve is used to push an implantable medical device out of, or simply away from, the distal end of the catheter. Handles, knobs, or other manually operated control means are attached to the opposite end of the guidewire or inner sleeve in the assembly.

Some implantable medical devices, such as stents and stent-grafts, often require reconfiguration from an initial compacted form to an expanded cylindrical configuration as the device is deployed at an implantation site. These devices can expand on their own by virtue of the design and composition of their structural elements or through the use of an inflatable balloon placed inside the devices.

Interventional medical devices are maintained in a compacted configuration in a variety of ways. Some devices are maintained in a compacted configuration by simply confining the compacted devices inside a catheter, or similar tool. Other devices are held in a compacted configuration with a removable line of material threaded through structural elements of the devices. These devices are free to expand when the drawstring is withdrawn from the structural elements of the devices. Yet other devices are placed inside a removable or breachable sheath following compaction. In these devices, the sheath is usually removed or breached by pulling on a drawstring, or similar control line, attached to the sheath.

U.S. Pat. No. 6,352,561, issued to Leopold et al., teaches the use of a control line made of a polytetrafluoroethylene suture material to initially close a restraining member around a self-expandable medical device. The sheath-like restraining member is closed around the self-expanding medical device by bringing opposite sides of a planar restraining member together in the form of a tube and stitching the control line along the length of the restraining member to form a seam. In preferred embodiments, the control line is stitched in a chain-stitch pattern that permits the control line to become unstitched from the restraining member when pulled upon by a practitioner. As the control line becomes unstitched from the restraining member, the self-expanding medical device begins to expand and displace the restraining member from around the device. When porous polytetrafluoroethylene materials are used for the control line, force exerted on the control line by the self-expanding medical device following release of the first few chain-stitches can cause the control line to become unstitched along portions of the restraining member without pulling on the control line any further. While the lubriciousness and biocompatibility of porous polytetrafluoroethylene control lines are desirable in this application, it would be advantageous to decrease the tendency of a porous polytetrafluoroethylene control line to become unstitched from a restraining member by the forces of an expanding medical device. A control line having more tensile strength, higher modulus and structural rigidity, and/or less compressibility than a porous polytetrafluoroethylene control line would cause the control line to become released from the restraining member only when the control line is pulled by a practitioner. This would provide a practitioner with more control over the release of the control line from the restraining member. Indeed, such a control line would provide a practitioner with tactile feedback through the control line of the release of each chain-stitch. Such a control line could be provided with a lubricious, biocompatible, fluoropolymer covering and maintain its desired stitch retaining properties.

It would also be advantageous to use a control line with as small a diameter as practical in order to reduce the size and increase the flexibility of the catheter component of an implant assembly.

An implantable medical device assembly that would achieve these advantages would utilize a control line having a small diameter core made of a high tensile strength non-fluoropolymer material surrounded by a fluoropolymer material.

SUMMARY OF THE INVENTION

The present invention is directed to an implantable medical device assembly. The assembly includes an expandable element in the form of an interventional, endovascular, or other implantable device. The assembly is provided with a means for passing the expandable element through the body of an implant recipient to an implantation site. These means usually take the form of a catheter or other hollow tubular construct. In some embodiments, the catheter, or other means, is used to house the expandable element. The device assembly can be provided with a guidewire to assist in positioning and deployment of the expandable element. As an alternative to a guidewire, the catheter, or other means, can be supplied with an inner tube-like member that can slide back and forth within the catheter. The tube-like member is usually used to push the expandable element out of the end of the catheter to deploy the element at an implantation site.

The assembly is provided with at least one removable control line. The control line leads from the expandable element located at the distal end of a catheter through the catheter to the proximal end where it connects to a control means, such as a knob or handle. The assembly has means for maintaining the expandable element in a compacted, collapsed, or otherwise compressed configuration. In one embodiment, the expandable element is maintained in a compacted configuration by attaching the control line to structural elements of the expandable element. In another embodiment, the expandable element is confined in a compacted configuration with confinement means in the form of a sheath or other external constraint. The control line is used to hold the confinement means together around the expandable element. The control line is attached to the expandable element and/or confinement means by threading, or sewing, the control line in a pattern that permits the control line to be readily removed from the element or confinement means by simply pulling on the control line. When used with a confinement means, the control line can be attached to the sheath in such a way that the control line can be used to retrieve the confinement means from the implantation site.

The control line has a core made of a non-fluoropolymer material and a cover surrounding the core made of a fluoropolymer material. The non-fluoropolymer core material has high tensile strength. The high tensile strength core allows the fluoropolymer-covered control line to be have higher tensile strength, a higher modulus, more structural rigidity, and/or less compressible than a control line made of a porous fluoropolymer material alone. These properties enable the control line to resist the tendency of porous fluoropolymer control lines to become unstitched by forces exerted on the control line by a self-expanding medical device as the device is released from a constraint.

The high tensile strength core also allows the control line to have a smaller diameter and greater break-strength than conventional drawstrings and device constraints. The fluoropolymer cover provides the control line with an outer surface that is biologically inert. The fluoropolymer material also provides the control line with a lubricious surface. The lubricious surface helps minimize the pulling forces required to operate the control line during deployment of the expandable element from the implantable device assembly. By minimizing the pulling forces imposed on the control line, the diameter of the control line can be made even smaller.

In some embodiments, the fluoropolymer material is in a porous form. Introducing pores into a fluoropolymer material increases the flexibility of the material and the resulting control line. The pores optionally provide reservoirs for a variety of substances. Some substances can contribute further to the lubriciousness of the fluoropolymer cover. Other substances can be palliative or of therapeutic benefit to the implant recipient. Yet other substances can provide diagnostic information.

In other embodiments, the non-fluoropolymer core material may have void spaces that can serve as reservoirs for various substances. As with the fluoropolymer material, the substances can be palliative or of therapeutic benefit to the implant recipient.

In addition to imparting greater flexibility to the present implantable medical device assembly, the control line is sufficiently resistant to becoming unstitched from an expandable element, confinement means, or other constraint that enhanced tactile feedback is perceived through the line. With many procedures, a practitioner can feel individual stitches, knots, or other tie-downs, being released as the control line is manually operated.

A preferred embodiment of the present invention is an implantable medical device assembly comprising an expandable element, at least one control line removably attached to the implantable device assembly, the control line comprising a non-fluoropolymer core and a fluoropolymer cover surrounding the core.

Another embodiment of the present invention is a medical device assembly comprising an implantable device, at least one non-implantable control line removably attached to the implantable device, wherein the control line comprises a non-fluoropolymer core and a fluoropolymer material surrounding the core.

Yet another embodiment of the present invention is a medical device assembly comprising an implantable device having a cover placed on at least a portion of the device, at least one non-implantable control line removably attached to the cover, wherein the control line comprises a non-fluoropolymer core and a fluoropolymer material surrounding the core.

These enhanced features and other attributes of the implantable medical device assembly of the present invention are better understood through review of the following specification.

BRIEF DESCRIPTION OF THE DRAWINGS

FIGS. 6A–6F sequentially illustrate the placement of an expandable element within a confinement means.

FIGS. 8A–8D sequentially illustrate progressive removal of a control line from an implant assembly of the present invention. The Figures also illustrate opening of a confinement means and expansion of an expandable element. The Figures show the control line being pulled by a mechanical arm of a test instrument.

DETAILED DESCRIPTION OF THE INVENTION

The present invention is directed to assemblies for implanting medical devices in implant recipients. The medical devices can be implanted in a recipient for a short term, a long term, or permanently. The assemblies are often used to introduce an expandable element into the vasculature of an implant recipient. The expandable element is in a compacted configuration when the assembly is introduced into the vasculature. The assembly of the present invention is then used to route the expandable element through the vasculature and deposit the element at an endovascular implantation site. The expandable element is deposited at the implantation site by manually operating a control line that releases the element from confinement in the compacted configuration. Following deployment of the expandable element at the implantation site, the remainder of the assembly is removed from the vasculature of the implant recipient.

Figure 5A:
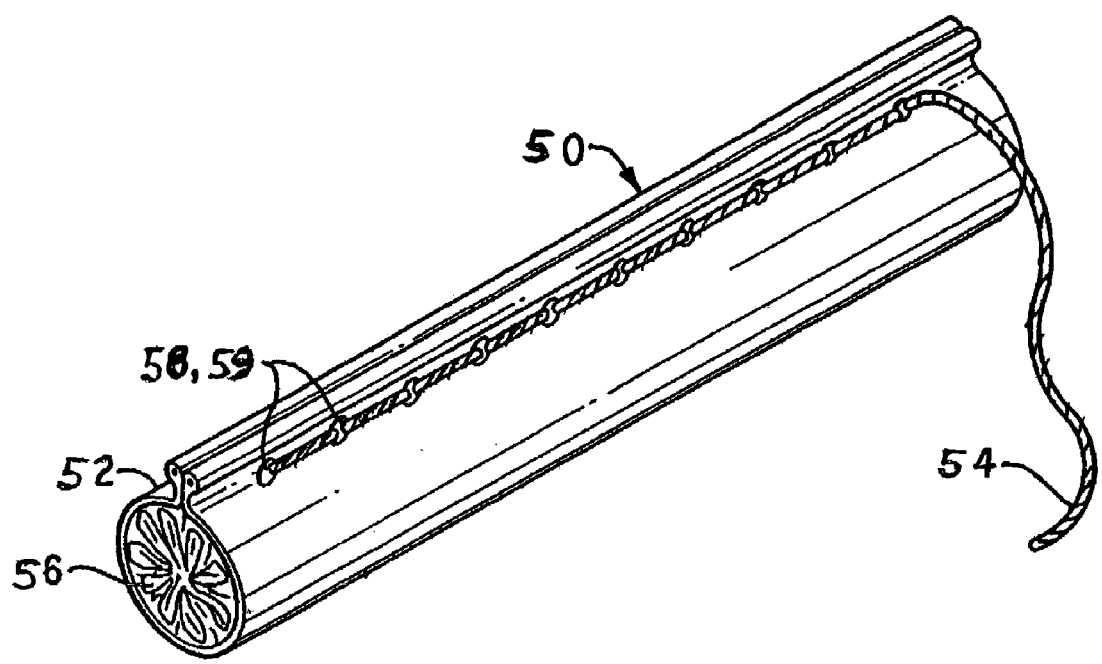
FIG. 5A illustrates a perspective view of an expandable element in a compacted state and contained within a confinement means. The confinement means are maintained around the compacted expandable element with a removable control line of the present invention.
Figure 5B:
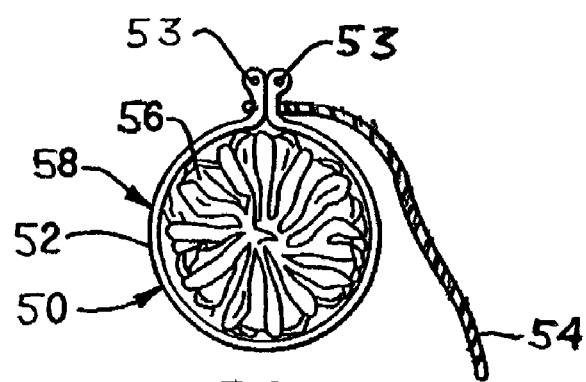
FIG. 5B illustrates an end view of the embodiment of FIG. 5A.
Figure 6A:
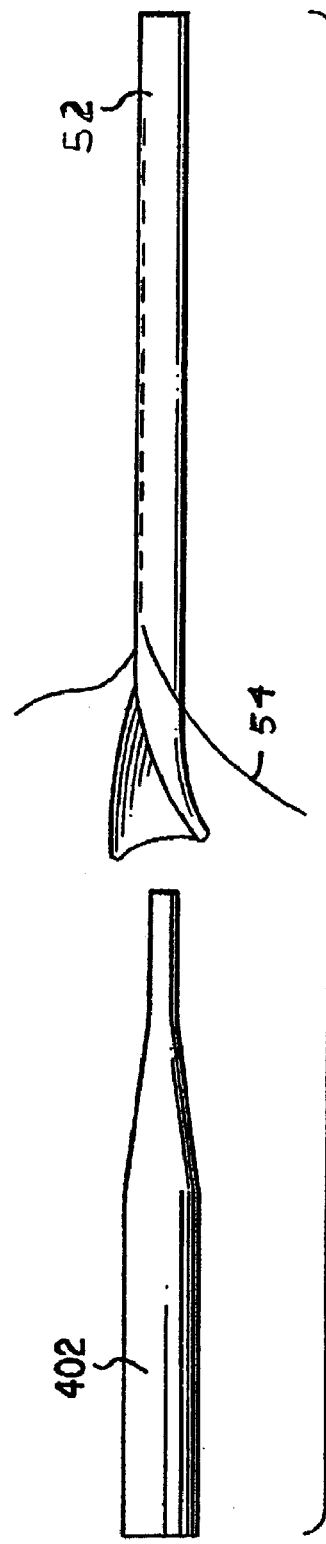
Figure 6B:
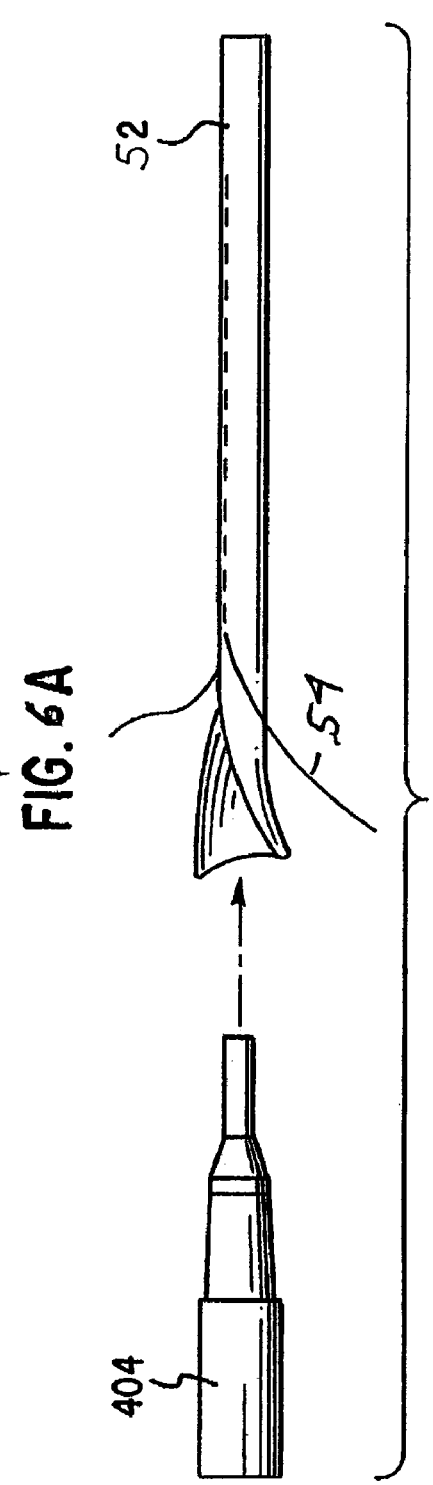
Figure 6C:
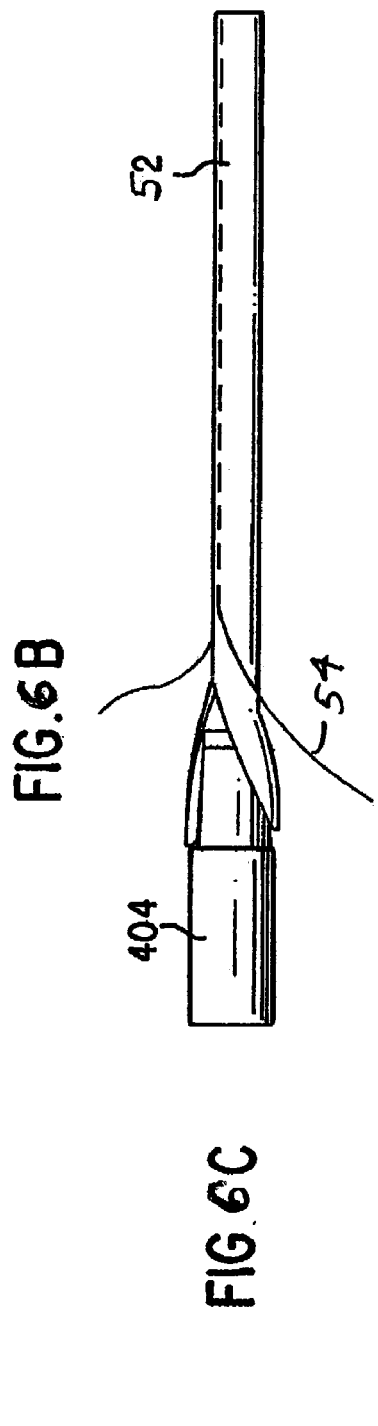
Figure 6G:
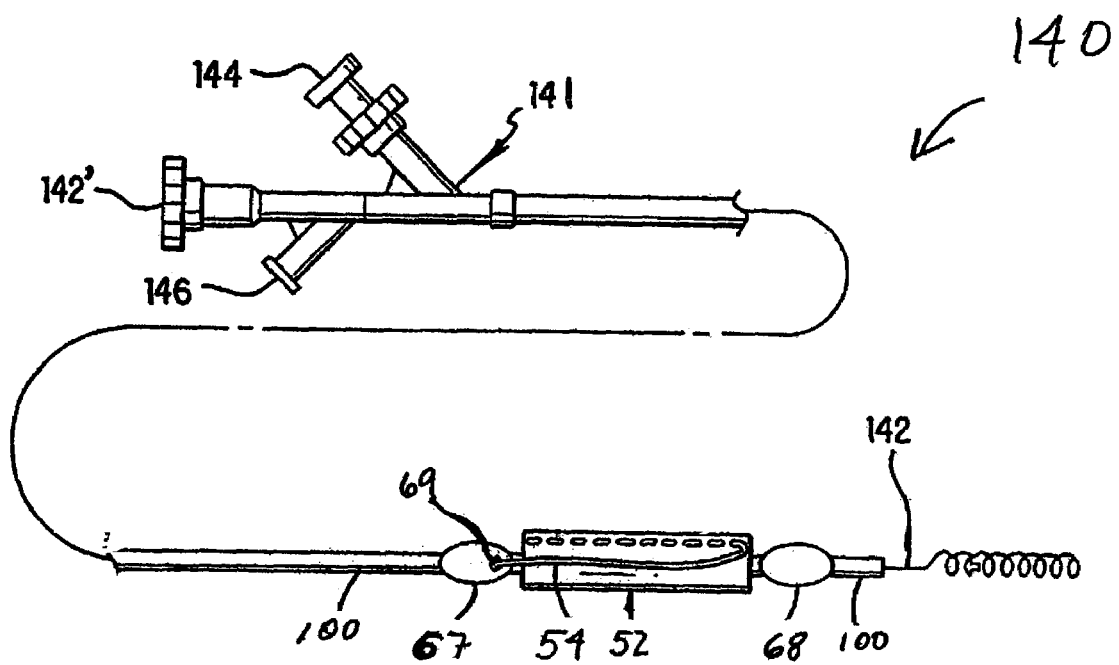
FIG. 6G illustrates a side view of the present invention.

As seen in FIG. 6G, the assembly of the present invention (140) has a delivery means (100) in the form of a delivery catheter. A control means (141) in the form of a hub having an access, or flushing, port (146), control knob (144) and valve (142') is attached to one end of the delivery means. An expandable element (FIGS. 5A and 5B, 56) is compacted and placed inside a confinement means (52) as shown in FIGS. 6A–6F. In this process the expandable element is attached to the opposite end of the delivery means. Barrier elements (67, 68) are placed on the proximal and distal ends, respectively, of the expandable element to assist in confining the element to the delivery means. The confinement means (52) is provided with a removable control line (54) that initially maintains the confinement means (52) around the expandable element (56) and subsequently releases the confinement means (52) from around the expandable element. The control line (54) is stitched to the confinement means (52) with a removable chain-stitch and threaded through an aperture (69) in proximal barrier element (67) and into delivery means (100). The control line (54) continues through the delivery means (100) to the control means (141) where the control line (54) is attached to control knob (144). A guidewire (142) is optionally provided from the expandable element (56) through the delivery means (100) and connected to a valve (142').

The expandable element is preferably in the form of an endovascular device. Endovascular devices often are characterized by metal frameworks with designs and compositions that permit the prostheses to be initially compacted, collapsed, or otherwise reduced in profile and subsequently enlarged in profile at an implantation site to an expanded configuration. The expandable element is often enlarged in profile with an inflatable balloon placed inside the expandable element. Other expandable elements are made of materials that can store mechanical energy and expand the profile of the prostheses without the need for a balloon or other tool. Preferred materials for these "self-expanding" prostheses are metal alloys made of nickel and titanium. These "nitinol" metals have a characteristic commonly referred to as "superelasticity." The most preferred expandable elements have coverings of polymeric materials. The polymeric coverings fill spaces between framework elements. When substantially all of the spaces between framework elements are covered, the expandable elements are able to conduct fluids, including blood. Preferred polymeric materials include, but are not limited to, polyesters, NYLON® fabric (i.e., any of a family of high-strength, resilient synthetic polymers, the molecules of which contain the recurring amide group CONH), and fluoropolymers such as polytetrafluoroethylene. The most preferred polymeric covering material is porous expanded polytetrafluoroethylene. Exemplary expandable elements in the form of endovascular prostheses include, but are not limited to, the EXCLUDER™ Bifurcated Endoprosthesis, the EXCLUDER™ Thoracic Endoprosthesis, and the VIABAHN™ Endoprosthesis. Other expandable elements are in the form of non-vascular prostheses such as the VIABAHN™ Biliary Endoprosthesis and the VIATORR™ TIPS Endoprosthesis. Each of these devices is available from the Medical Products Division of W.L. Gore & Associates, Inc., Flagstaff, Ariz.

In other embodiments, the expandable element is in the form of an occluder, closure device, and/or diagnostic device.

The expandable element (56) is incorporated into the assembly by placing a compacted, collapsed, or folded expandable element (56) over the delivery means (100). In some embodiments, a control line is threaded through the structural elements of a collapsed expandable element as a means for maintaining the expandable element in the collapsed configuration. In other embodiments, the control line is wrapped around the collapsed expandable element. In the preferred embodiment, a means for confining, or maintaining, the expandable element in a collapsed configuration is attached or applied to the expandable element prior to placing the expandable element over the delivery means. In the preferred embodiment, the expandable element is compacted and placed inside a confinement means (52). In this embodiment, a control line (54) is used to maintain the confinement means around the expandable element. The control line (54) also serves as a means for releasing the confinement means (52) from the expandable element (56).

The confinement means (52) is preferably in the form of a tube, or hollow cylinder. The tubular form is made from a sheet of a biocompatible polymeric material. The sheet material is sized to substantially, or entirely, enclose the expandable element. In the preferred embodiment, the sheet material is in the form of a rectangle. A reinforcing thread (53), or filament, is placed along both of the long edges of the rectangular sheet material. The preferred reinforcing filament is a porous polytetrafluoroethylene material in the form of a thread or suture. The reinforced edges of the sheet material are brought together to form a tubular structure. The reinforced edges of the sheet material are held together with a control line (54) of the present invention. The control line (54) is sewn adjacent to the reinforced edges of the sheet material in a chain-stitch pattern (FIGS. 3A, 3B, and 4) to form a removable seam along the length of the confinement means (52). The expandable element (56) is then placed inside the tubular confinement means (FIGS. 6A–6F). The sheet material for the confinement means can be any biocompatible polymeric material of sufficient strength to confine the expandable element and of sufficient compliance to be routed through the vasculature of an implant recipient. Suitable materials for the confinement means of the present invention are the same as, or similar to, those described above for covering an endovascular prosthesis. Preferred materials are fluoropolymers. Preferred fluoropolymers are polytetrafluoroethylene (PTFE) materials. The preferred PTFE materials are porous expanded polytetrafluoroethylene materials (ePTFE).

Referring to FIGS. 6A through 6F, a method for making an assembly comprising a restraining member with a collapsed or compressed implant therein is shown for purposes of example. FIG. 6A shows the confinement means (52) with its side margins releasably coupled to one another with a removable control line (54) and its left end dilated by a tapered mechanical dilator (402). A small funnel (404) is then inserted into the confinement means (52) as shown in FIGS. 6B and 6C. The small funnel (404) and confinement means (52) are then mounted onto a pulling frame (410), and a large funnel (406) is fitted into the small funnel (404) as shown in FIG. 6D. Traction or pull lines (408), which have been sutured to one end of the expandable element, (56) are pulled through the large funnel (406), small funnel (404), and confinement means (52) with a tapered mandrel (416). As shown in FIG. 6F, the pull lines (408) are fastened to a tie down post (412) located on a tension screw (414) and then are pulled by the tension screw (414). The expandable element (56) is then pulled and collapsed sequentially through the large (406) and small (404) funnels, and then into the confinement means (52). Once the expandable element (56) has been radially collapsed into the confinement means (52), which has its side margins coupled together, the pull lines (408) can be removed. The mandrel (416) may be inserted into the restrained implant to facilitate introduction of another component. In the preferred embodiment, a delivery means (100) in the form of a multilumen catheter (FIG. 6G) is introduced through the center of the compressed expandable element (56) and is used to deliver the radially restrained expandable element (56) to the desired endolumenal site.

It also is noted that the funnels may be chilled to facilitate compression of the expandable element when the expandable element is made of nitinol. That is, when the expandable element is made of nitinol, the funnels may be chilled below 0° C. or below the transition temperature (Mf) where nitinol is in its martensitic state. In addition, the expandable element could be folded first and then reduced in profile by pulling through the funnel and into the confinement means. Cooling may be accomplished by spray soaking the expandable element with chilled gas such as tetrafluroethane. Micro-Dust™ dry circuit duster manufactured by MicroCare Corporation (Conn) provides suitable results. The spray canister preferably is held upside down to discharge the fluid as a liquid onto the expandable element.

Figure 4:
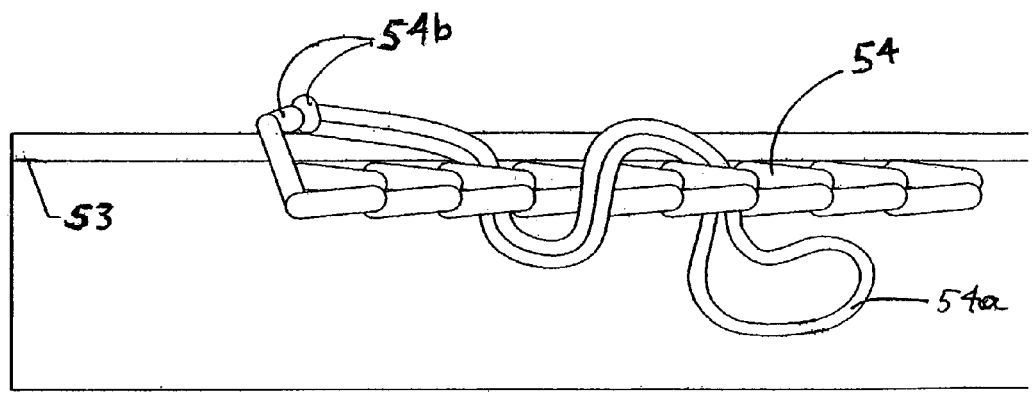
FIG. 4 illustrates a top view of the chain-stitching pattern used to removably attach the control line of the present invention to a confinement means.

A length of control line (54) is retained from the construction of the confinement means (52) to secure the chain-stitched portion of the control line (54) to the confinement means (52). As illustrated in FIG. 4, a loop (54a) is made in a portion of the length of control line (54) and two slip knots (54b) made at the base of the loop (54a). The loop (54a) is threaded underneath one or more of the chain-stitches as shown in FIG. 4. A clip, or other retaining means, is placed on the free end of the loop (not shown) to prevent the loop from being removed from underneath the chain-stitches prior to packaging or use.

The length of control line remaining from the loop is used as a means for removing the confinement means (52) from the expandable element (56). The free end of the control line is doubled back on the confinement means (52) and threaded through an aperture (69) in the proximal barrier element (67) and into a lumen of the delivery means (100). The control line (54) exits the delivery means (100) and enters a hub (141). The control line (54) is attached to a control knob (144) in the hub (141) by potting with an appropriate adhesive.

Figure 1:
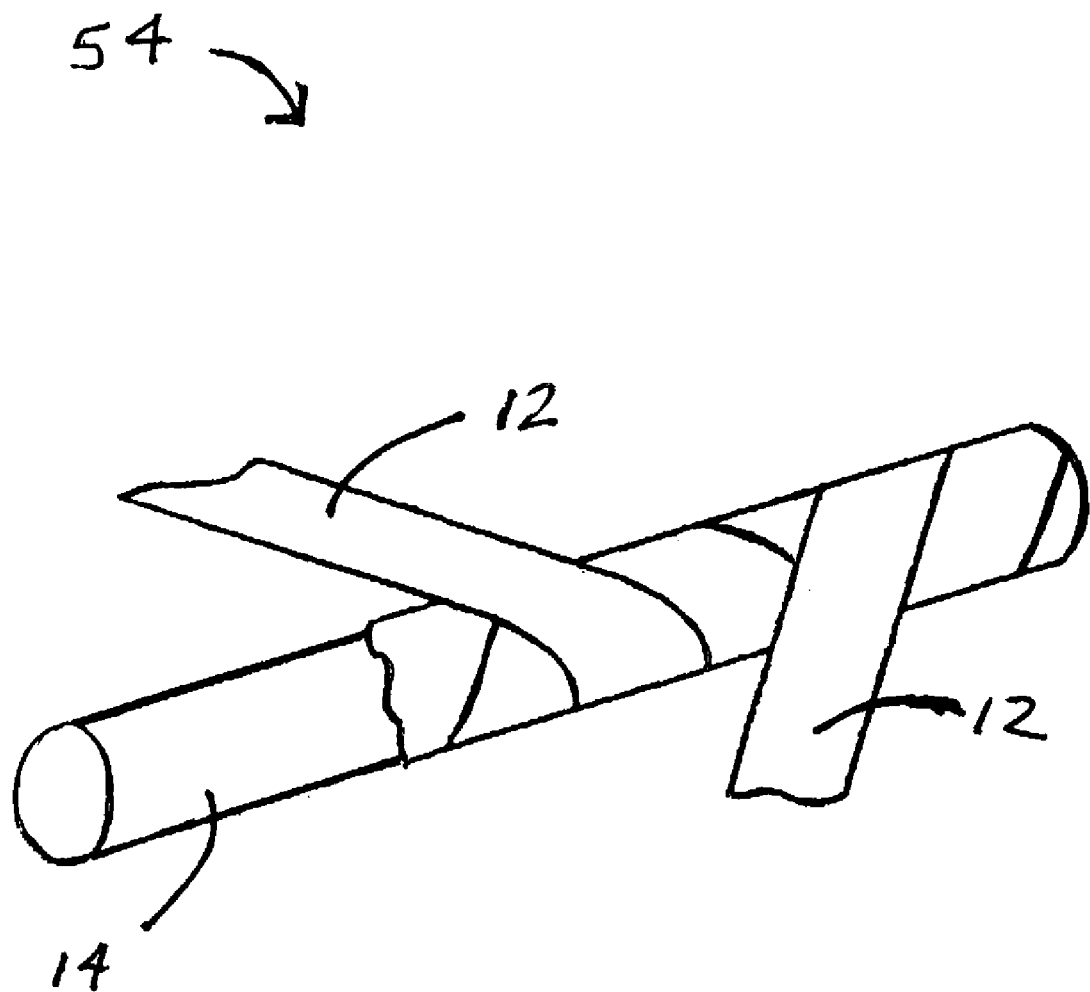
FIG. 1 illustrates perspective view of a control line of the present invention.

Shown in FIG. 1 is a partial section of the control line (54). The control line (54) is made of a non-fluoropolymer core material (14) surrounded by a fluoropolymer cover (12). The non-fluoropolymer core material (14) has high tensile strength, sufficient flexibility to course through mammalian vasculature, and low compressibility. The core material can be in the form of a mono-filament or a multi-filament. Preferred non-fluoropolymer materials include, but are not limited to, polyaramid fibers, liquid crystal polymers, including polyester-polyarylate, polyester, polyolefin, and polyamids. As used herein, non-fluoropolymer materials do not include metals. Accordingly, the core material (14) of the control line (54) is non-metallic in addition to being non-fluoropolymeric in composition.

Figure 2:
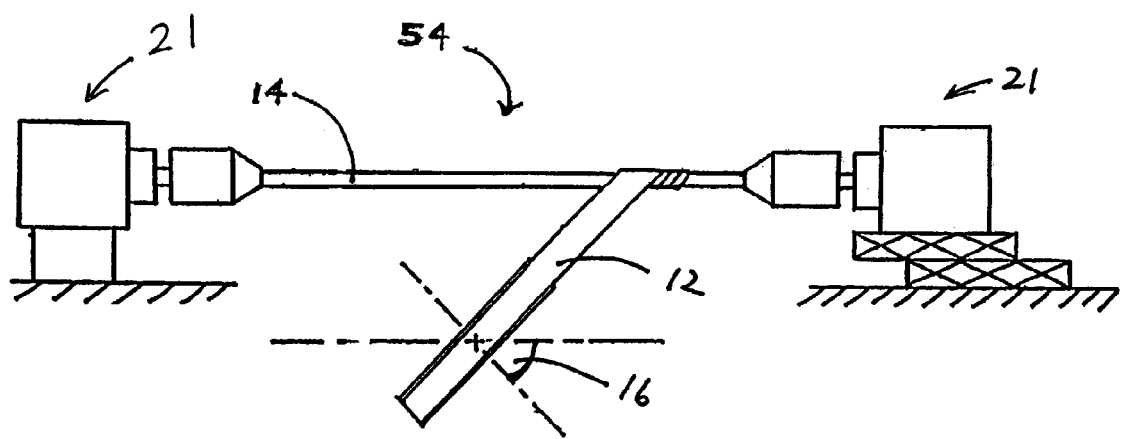
FIG. 2 illustrates a side view of a control line of the present invention during construction.

The fluoropolymer cover (12) can be made of fluorinated ethylene-propylene, perfluoroalkoxy, polyvinylidene, or ethylene terafluoroethylene. These materials can be combined together and/or blended with thermoplastic elastomers. The fluoropolymer cover (12) is preferably made of a polytetrafluoroethylene material. As described in greater detail in Example 1, below, polytetrafluoroethylene is expanded and formed into an ePTFE film or tape for wrapping around the non-fluoropolymer core material (14). The ePTFE film is preferably wrapped around the non-fluoropolymer core material in a helical pattern (FIG. 1). An apparatus (21) for applying the ePTFE film to the non-fluoropolymer core material in a helical pattern is illustrated in FIG. 2. The ePTFE film (12) is applied to the core (14) at an angle (16) as the core (14) is rotated by the apparatus (21).

In addition to wrapping a fluoropolymer material around a non-fluoropolymer core, the non-fluoropolymer core can be covered with a fluoropolymer material by paste extrusion, dip coating, spray coating, solvent coating, plasma coating, or hot melt extrusion.

To deploy an expandable element at an endovascular implantation site, the expandable element is released from the confinement means by operating the control line. The control line is operated by unscrewing knob (144) from hub (141) and manually pulling on control line (54). As the removable control line (54) is manually pulled, the slip-knots are untied, the loop removed, and the chain-stitches of the confinement means sequentially unstitched. When the entire control line becomes unstitched from the confinement means, the control line is considered removed from the implant assembly.

The control line of the present invention initially requires a greater pulling force to begin removal of the control line from the confinement means than a control line made of ePTFE alone. Despite the greater initial pulling force, the control line of the present invention does not become unstitched from the confinement means as the expandable element expands and presses against any remaining stitched portions of the confinement means. As a result, essentially every stitch in the confinement means must be removed one stitch at a time. This is an advantageous property of the control line of the present invention because a practitioner can control the release of individual stitches from the confinement means. As a practitioner begins to remove an individual chain-stitch from the confinement means, an increase in manually applied force is required to initiate movement of the control line through the loop portion of the stitch. The practitioner can feel this increase in force. As the control line is pulled through the loop and the chain-stitch removed from the confinement means, the resistance to the movement of the control line exerted by the chain-stitch sharply diminishes. This decrease in resistance is transmitted through the control line and perceived by the practitioner as a momentary "freeing" of the control line. As the control line is advanced to the next chain-stitch, the force required to begin removal of the control line from the chain-stitch increases. The practitioner can feel this increase in force also. An oscillating cycle of increasing and decreasing forces is generated through the control line as individual chain-stitches are removed from the confinement means. The perception of these oscillating forces by a practitioner is referred to herein as "tactile feedback."

Figure 10:
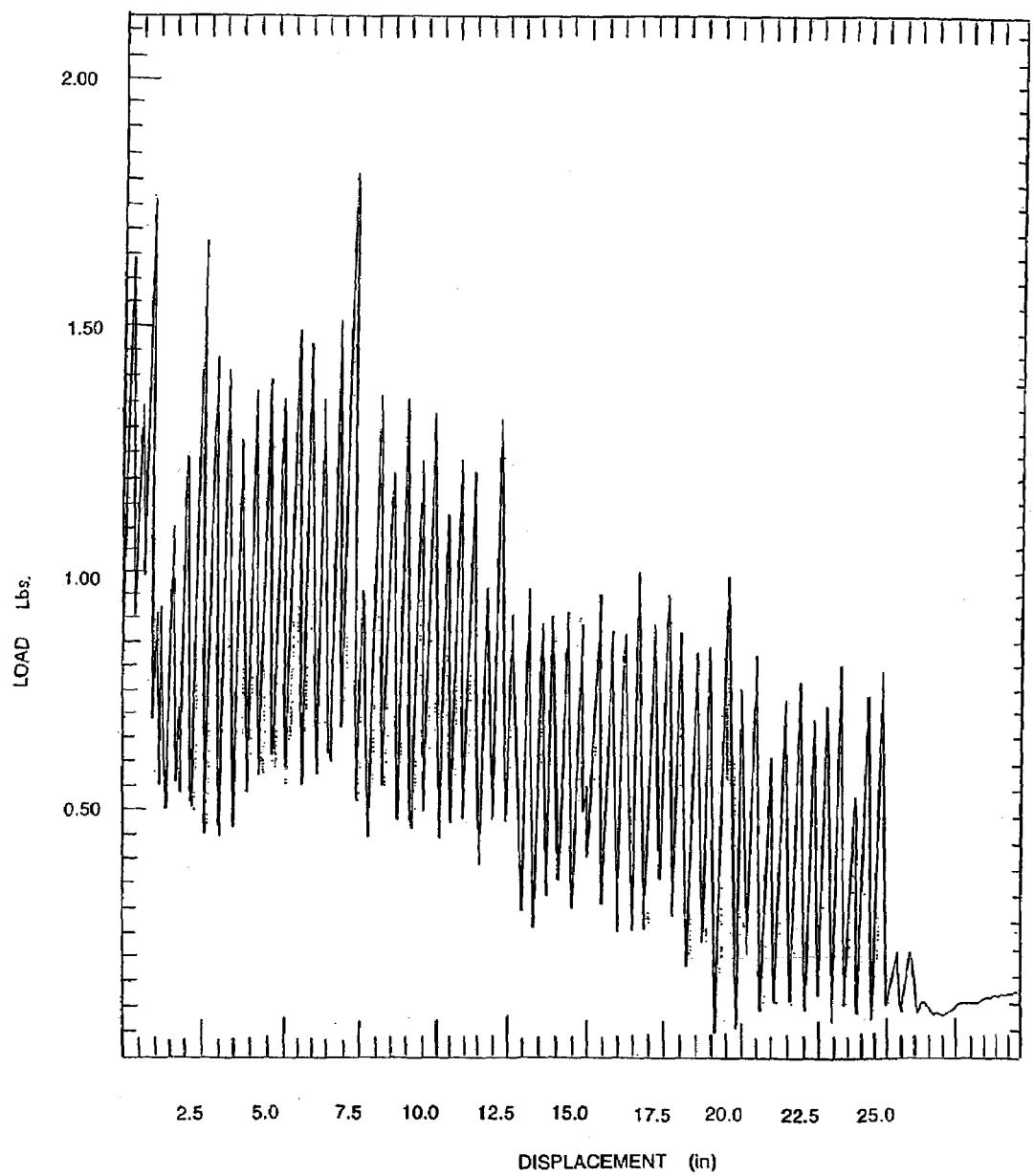
FIG. 10 is a graph showing a force to displacement relationship for a control line of the present invention as the control line is operated in an implant device assembly by a test instrument.

The presence of tactile feedback in an assembly of the present invention is illustrated in the graph of FIG. 10. The graph was generated with a testing apparatus and method described in Example 4, below. The graph shows the relationship between the amount of force applied to the control line in an assembly of the present invention and the length of control line removed from the assembly. The graph shows an increase in force initially applied to the control line as the first stitch in the chain begins to be removed from the chain-stitch. A decrease in force is seen when the stitch is removed from the chain. The cycle of increasing and decreasing forces applied to the control line repeats throughout the removal of the control line from the confinement means. The oscillating forces recorded through a mechanical arm of the test apparatus represent the same oscillating forces perceived by the hand of a practitioner as tactile feedback.

Figure 9:
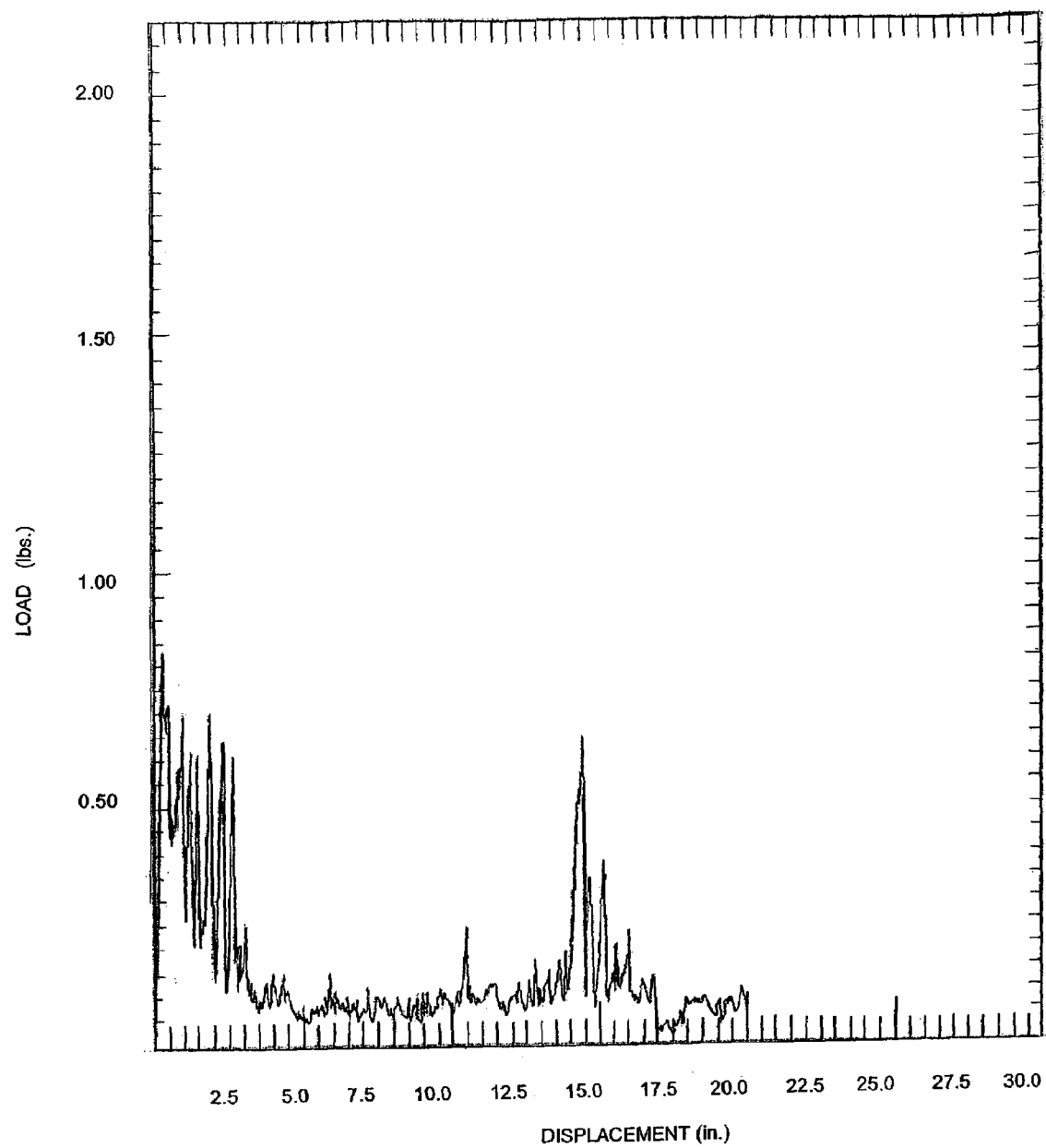
FIG. 9 is a graph showing a force to displacement relationship for a porous polytetrafluoroethylene control line as the control line is operated in an implant device assembly by a test instrument.

The absence of tactile feedback with an ePTFE control line is illustrated in the graph of FIG. 9. The graph was generated with a testing apparatus and method described in Example 4, below. The graph shows the relationship between the amount of force applied to an ePTFE control line and the length of control line removed from the assembly. The graph shows an increase in force initially applied to the control line as the first stitch in the chain begins to be removed from the chain-stitch, but of lesser magnitude than the control line of the present invention. A decrease in force is seen when the stitch is removed from the chain. A cycle of increasing and decreasing forces applied to the control line is seen for only the first few stitches. After the first few stitches are removed from the confinement means, forces exerted on the control line by the expanding expandable element tend to cause the remaining stitches to become unstitched without pulling any further on the ePTFE control line. As a result, very little, if any, tactile feedback is experienced by a practitioner when an ePTFE control line is used in the implant assembly.

EXAMPLES

Example 1

This example describes the construction of a control line component of the present invention (FIG. 1, part 54). The control line comprises a non-fluoropolymer core material (14) covered with a fluoropolymer material (12).

The non-fluoropolymer core material was in the form of a 400 denier polyaramid fiber available from Saunders Thread Company, Gastonia, N.C. under the tradename KEV-LAR® brand fiber. This fiber was identified by Saunders Thread Company as SK1(x) Natural NF.

The covering for the fiber was made of a thin, high strength, stretched, non-woven web of polytetrafluoroethylene composed substantially of nodes interconnected by fibrils (ePTFE). The film was made as generally taught by Bacino in U.S. Pat. No. 5,476,589. The method includes providing a PTFE fine powder with a low amorphous content and a degree of crystallization of at least 98% was used as the raw material. This PTFE fine powder was made into a paste by uniformly mixing it with an extrusion aid of a mineral spirit, naphtha, or other such lubricant. This paste was then molded into the shape dictated by the intended use of the finished product by a molding method that imparts shear deformation, such as extrusion molding or calender molding. The paste was molded into the form of a tape by extrusion.

The polytetrafluoroethylene used herein was coagulated dispersion or fine powder polytetrafluoroethylene. Several such resins that have been used demonstrate that the various commercially available fine powders from the several suppliers of such resins are suitable in the process. Some such resins can tolerate more extrusion aid than others and still yield products within the range of permeability desired. Some such resins suitable for use are DAIKIN-POLY-FLON™ polytetrafluoroethylene available from Daikin America, Inc. Decatur, Ala. The coagulated dispersion powders were lubricated with a hydrocarbon extrusion aid, preferably as odorless mineral spirit such as Isopar K (made by Exxon Corp.). The lubricated powder was compressed into cylinders and extruded in a ram extruder to form tapes. Two or more layers of tape can be stacked together and compressed between two rolls. The tape or tapes were compressed between rolls to an appropriate thickness, e.g. 5 to 40 mils, or so. The wet tape was stretched traversely to 1.5 to 5 times its original width. The extrusion aid was driven off with heat. The dried tape was then expanded longitudinally between banks of rolls in a space heated to a temperature that was below the polymer melting point (327° C.). The longitudinal expansion was such that the ratio of speed of the second bank of rolls to the first bank was 10–100 to 1. The longitudinal expansion was repeated at a 1–1.5 to 1 ratio.

Next, the tape, after the longitudinal expansion, was expanded traversely at a temperature that was less than 327° C. to at least 1.5 times and preferably to 6 to 15 times the input width of the original extrudate while restraining the membrane from longitudinal contraction. While still under constraint, the membrane was heated to above the polymer melting point (327° C.) and then cooled. The resulting ePTFE film had a thickness of about 0.005 mm (0.0002 inches). The film was then provided with a continuous coating of fluorinated ethylene propylene (FEP) polymer adhesive on one surface.

FEP was applied to the ePTFE as generally described by Leopold et al., in U.S. Pat. No. 6,352,561 by a process that comprises the steps of:

(a) contacting a porous PTFE film with another layer which is preferably a film of FEP or alternatively of another thermoplastic polymer;

(b) heating the composition obtained in step (a) to a temperature above the melting point of the thermoplastic polymer;

(c) stretching the heated composition of step (b) while maintaining the temperature above the melting point of the thermoplastic polymer; and (d) cooling the product of step (c).

In addition to FEP, other thermoplastic polymers including thermoplastic fluoropolymers may also be used to make this coated film. The adhesive coating on the porous expanded PTFE film may be either continuous (non-porous) or discontinuous (porous) depending primarily on the amount and rate of stretching, the temperature during stretching, and the thickness of the adhesive prior to stretching.

Four layers total of the FEP-coated ePTFE film were applied to the polyaramid fiber at an angle (16) to form a helical wrapping pattern (FIG. 2). The first two layers of the film were applied to the fiber either in one direction or in opposite directions in the first pass. The angle, or pitch, of the film was applied to the fiber at 2.54 mm/revolution (0.1 inch/revolution) for the first pass. The width of the film used for the first pass was approximately 2 mm (0.08 inches). The other two layers of film were applied in the second pass either in one or opposite directions. The angle, or pitch, of the film was applied to the fiber at 3.3 mm/revolution (0.13 inch/revolution) for the second pass. The width of the film used for the second pass was approximately 2.3 mm (0.09 inches). Film tension for both passes was approximately 35 grams (0.08 lbf). After wrapping, the construct was placed into an apparatus that maintained the construct in a straightened configuration under tension. The construct was then placed into an oven with a setpoint of 330–380° C. for twenty to sixty seconds to melt the FEP and cause the ePTFE layers to become adhered together. The construct was allowed to cool.

Example 1A

This example describes the construction of a control line component of the present invention (FIG. 1, part 10). The control line comprises a non-fluoropolymer core material (14) covered with a fluoropolymer material (12). The non-fluoropolymer core material is in the form of a monofilament made of an aromatic polyester. Aromatic polyesters are also referred to herein as liquid crystal polymers. The liquid crystal polymer used in this example is available from Celanese Americas Corp., Summit, N.J. in the form of a multi-filament yarn spun from VECTRA® liquid crystal polymer (LCP). The yarn is sold under the tradename VECTRAN® Fiber.

The covering for the monofilament is made of a thin, high strength, stretched, non-woven web of polytetrafluoroethylene composed substantially of nodes interconnected by fibrils (ePTFE). The film is made as generally taught by Bacino in U.S. Pat. No. 5,476,589. The method includes providing a PTFE fine powder with a low amorphous content and a degree of crystallization of at least 98% is used as the raw material. This PTFE fine powder is made into a paste by uniformly mixing it with an extrusion aid of a mineral spirit, naphtha, or other such lubricant. This paste is then molded into the shape dictated by the intended use of the finished product by a molding method that imparts shear deformation, such as extrusion molding or calender molding. The paste is molded into the form of a tape by extrusion.

The polytetrafluoroethylene used herein is coagulated dispersion or fine powder polytetrafluoroethylene. Several such resins that are used demonstrate that the various commercially available fine powders from the several suppliers of such resins are suitable in the process. Some such resins can tolerate more extrusion aid than others and still yield products within the range of permeability desired. Some such resins suitable for use are DAIKIN-POLYFLON™ polytetrafluoroethylene available from Daikin America, Inc. Decatur, Ala. The coagulated dispersion powders are lubricated with a hydrocarbon extrusion aid, preferably as odorless mineral spirit such as Isopar K (made by Exxon Corp.). The lubricated powder is compressed into cylinders and extruded in a ram extruder to form tapes. Two or more layers of tape can be stacked together and compressed between two rolls. The tape or tapes are compressed between rolls to an appropriate thickness, e.g. 5 to 40 mils, or so. The wet tape is stretched traversely to 1.5 to 5 times its original width. The extrusion aid is driven off with heat. The dried tape is then expanded longitudinally between banks of rolls in a space heated to a temperature that is below the polymer melting point (327° C.). The longitudinal expansion is such that the ratio of speed of the second bank of rolls to the first bank was 10–100 to 1. The longitudinal expansion is repeated at a 1–1.5 to 1 ratio.

Next, the tape, after the longitudinal expansion, is expanded traversely at a temperature that was less than 327° C. to at least 1.5 times and preferably to 6 to 15 times the input width of the original extrudate while restraining the membrane from longitudinal contraction. While still under constraint, the membrane is heated to above the polymer melting point (327° C.) and then cooled. The resulting ePTFE film has a thickness of about 0.005 mm (0.0002 inches). The film is then provided with a continuous coating of fluorinated ethylene propylene (FEP) polymer adhesive on one surface.

FEP is applied to the ePTFE as generally described by Leopold et al., in U.S. Pat. No. 6,352,561 by a process that comprises the steps of:

(a) contacting a porous PTFE film with another layer which is preferably a film of FEP or alternatively of another thermoplastic polymer;

(b) heating the composition obtained in step (a) to a temperature above the melting point of the thermoplastic polymer;

(c) stretching the heated composition of step (b) while maintaining the temperature above the melting point of the thermoplastic polymer; and (d) cooling the product of step (c).

In addition to FEP, other thermoplastic polymers including thermoplastic fluoropolymers may also be used to make this coated film. The adhesive coating on the porous expanded PTFE film may be either continuous (non-porous) or discontinuous (porous) depending primarily on the amount and rate of stretching, the temperature during stretching, and the thickness of the adhesive prior to stretching.

Four layers total of the FEP-coated ePTFE film are applied to the monofilament at an angle (16) to form a helical wrapping pattern (FIGS. 1 and 2). The first two layers of the film are applied to the monofilament either in one direction or in opposite directions in the first pass. The angle, or pitch, of the film is applied to the monofilament at 2.54 mm/revolution (0.1 inch/revolution) for the first pass. The width of the film used for the first pass is approximately 2 mm (0.08 inches). The other two layers of film are applied in the second pass either in one or opposite directions. The angle, or pitch, of the film is applied to the fiber at 3.3 mm/revolution (0.13 inch/revolution) for the second pass. The width of the film used for the second pass is approximately 2.3 mm (0.09 inches). Film tension for both passes is approximately 35 grams (0.08 lbf). After wrapping, the construct is placed into an apparatus that maintains the construct in a straightened configuration under tension. The construct is then placed into an oven with a setpoint of 330–380° C. for twenty to sixty seconds to melt the FEP and cause the ePTFE layers to become adhered together. The construct was allowed to cool.

Example 2

In this example, the construct described in Example 1 was measured for tensile strength using an Instron Tensile Testing Machine, model no. 4465 (Instron Corporation, Canton, Mass.). The overall diameter of the Example 1 construct was between 0.2 and 0.4 mm (0.009 and 0.014 inches). The test was conducted using a 10 kg. (22 lbf) load cell. The gauge length of each sample was 229 mm (9 inches) and the wrapped core assembly was held in the instrument using suture grips set at 0.35 MPa (50 psig). Testing was performed at a rate of 200 mm/min (8 inches/min). Per this test method, the wrapped core assembly exhibited a break-strength of approximately 6.8 kg (15 lbf).

Example 3

This example describes the use of the construct of Example 1 in a medical device assembly as taught by Leopold et al. in U.S. Pat. No. 6,352,561. The implant delivery system described by Leopold et al. includes an expandable stent-graft, delivery means in the form of a catheter, and confinement means for maintaining the stent-graft in a compacted, collapsed, or compressed configuration. The confinement means is in the form of a sheet material and a coupling member. The sheet material is in the shape of a tube that surrounds the compacted stent-graft. The coupling member is in the form of a filament or other thread-like element. The tube is held together with the coupling member. The coupling member releasably attaches one side of the sheet material to an opposite side of the sheet material by stitching the sides together with a removable stitch. The thread-like coupling member extends beyond the sheet material to form a remote control line. In preferred embodiments, the coupling member and control line are continuous. In the most preferred embodiments, the coupling member and control line are the same material. Pulling on the control line causes the coupling member to become unstitched. As the coupling member becomes unstitched, the stent-graft is released from the confinement means and allowed to expand.

In the present invention, the coupling member and control line are combined in a single construct. Accordingly, the means for maintaining a confinement means around an expandable element and releasing the expandable element from the confinement means is referred to herein as a "control line." The confinement means (52), expandable element (56), and control line (54) are illustrated in FIGS. 5A and 5B.

Figure 3A:
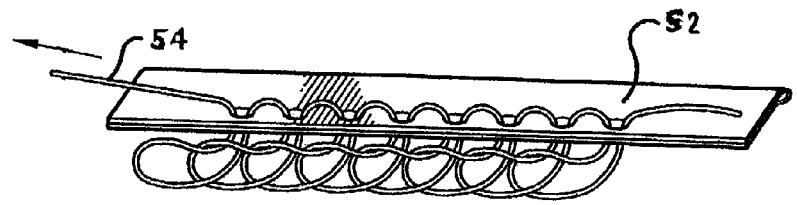
FIG. 3A illustrates a control line of the present invention removably attached to a confinement means.
Figure 3B:
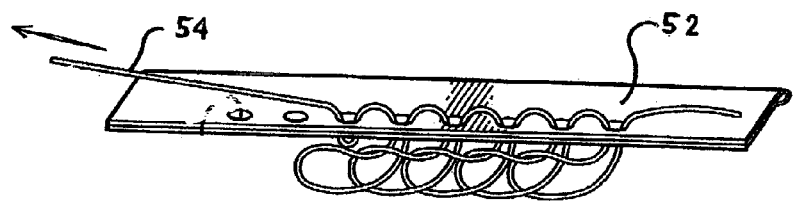
FIG. 3B illustrates the control line of FIG. 3A as the control line is being removed from the confinement means.
Figure 7A:
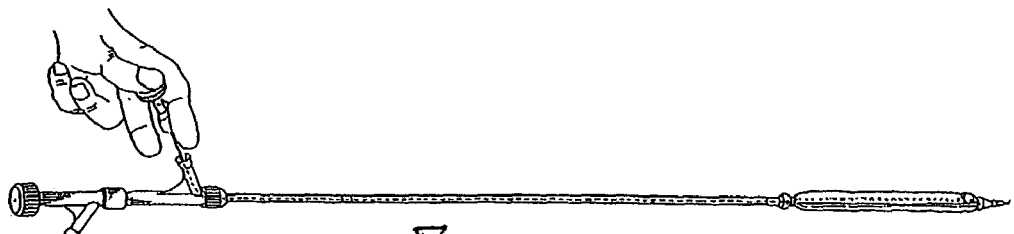
FIGS. 7A–7D sequentially illustrate progressive removal of a control line from an implant assembly of the present invention. The Figures also illustrate opening of a confinement means and expansion of an expandable element. The Figures show the control line being pulled by a hand of a practitioner.
Figure 7B:
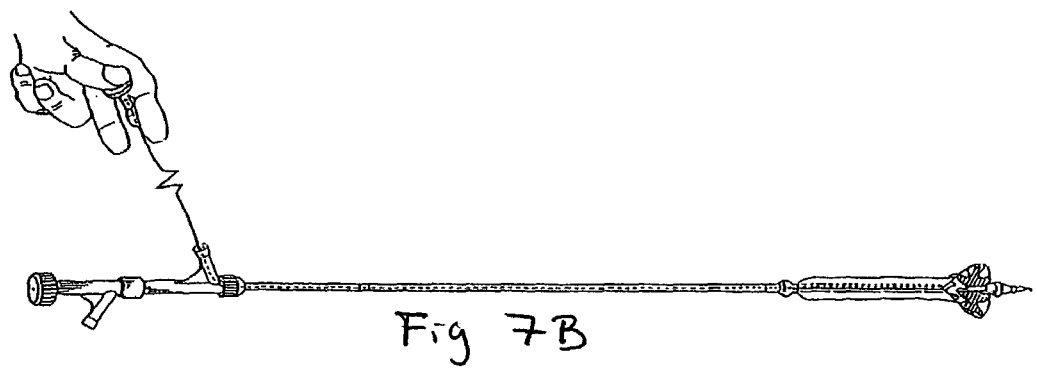
Figure 7C:
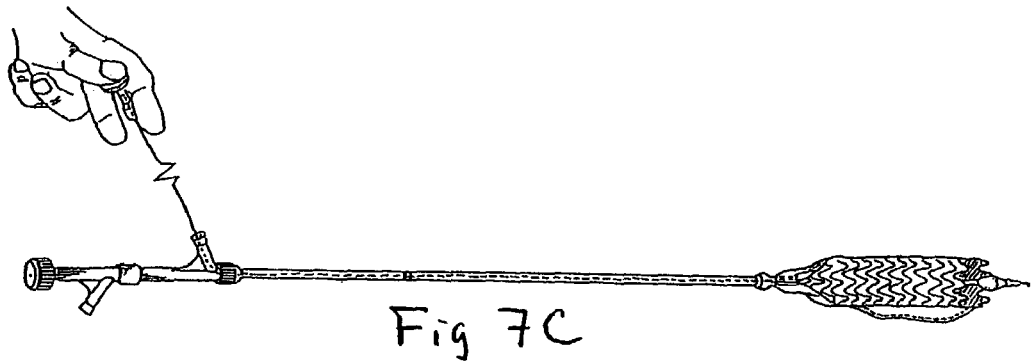
Figure 7D:
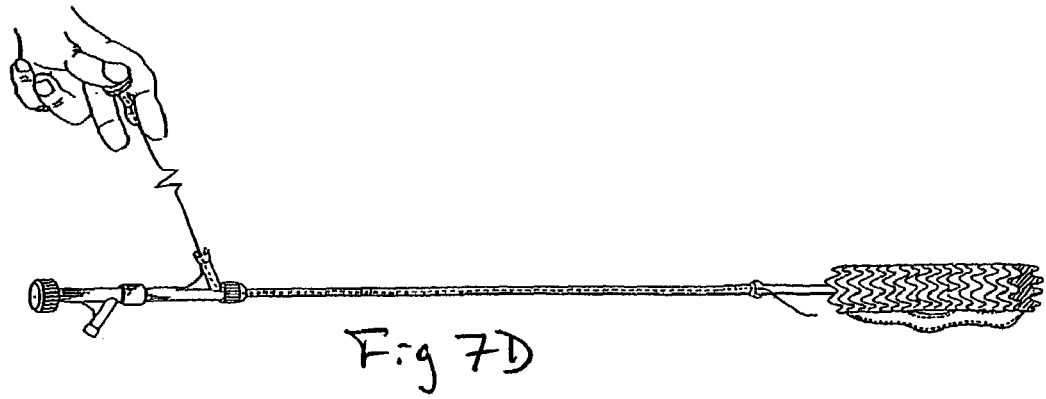

The control line is preferably attached to the confinement means with a stitch commonly referred to as a "chain stitch." The chain stitch maintains the sheet material around the compacted stent-graft. The chain stitch forms a series of loops or slip knots that are looped through one another so that one slip knot prevents the next slip knot from releasing until the control line is pulled upon (FIGS. 3A and 4). The chain stitches are preferably made with a single needle and a single length of the control line material described in Example 1. When the control line is pulled, the first slip knot in the series of chain stitches becomes undone and begins to release the next slip knot in the series (FIGS. 3B, 7A, and 8A). The process continues as the control line is pulled further until the entire control line is removed (FIGS. 7B–7D and 8A–8D). As described in Example 4 and illustrated in FIG. 10, the release of the control line occurs in a stepwise fashion. The stepwise release of the control line provides tactile feedback to a practitioner that allows for a more controlled and predictable removal of the control line from the implant assembly.

Example 4

This example compares the amount of pulling force required to unstitch a control line of the present invention from the assembly described in Example 3 with the amount of pulling force required to unstitch a control line made entirely of a polytetrafluoroethylene material used in the same assembly. Graphs showing a qualitative relationship between the amount of force applied to the control lines as the stitches are sequentially undone and the degree of displacement of the control lines from the assembly are shown in FIGS. 9 and 10. These curves are referred to herein as force/displacement curves.

The construct of Example 1 was compared in this example to a porous expanded polytetrafluoroethylene (ePTFE) control line of similar diameter in the form of a mono-filament available from W.L. Gore & Associates, Inc., Flagstaff, Ariz. under the tradename GORE-TEX® Suture as catalog number CV-5.

The control lines were compared by placing an implantable medical device assembly in a test apparatus designed to simulate an aortic aneurysm and pulling on the control line and the distal end of a guidewire supporting the assembly with an Instron 4501 testing machine. To perform the evaluation, a guidewire was threaded through a material that functions to seal an opening in the test apparatus similar to sealing an artery or vein in an implant recipient. The test apparatus was placed in a water bath maintained at 37° C. (±2° C.) to simulate human physiological temperatures. The implantable medical device assembly was flushed and filled with 37° C. (±2° C.) water. The water-filled device assembly was threaded over the guidewire (142) and advanced past the sheath and into the test apparatus. The confinement means (52) enclosing the expandable element (56) were positioned in the portion of the test apparatus representing an aneurysm. The device assembly is rotated in the test apparatus to confirm the moveable components of the assembly are free to move. A knob (144) attached to the control line was connected to one of two pneumatic grips of the Instron testing machine through a custom made jig. The control means (141) on the proximal end of the device assembly was attached to the other pneumatic grip of the testing machine.

Once the test apparatus and device assembly were properly prepared, the knob (144) attached to the control line (54) was loosened and software activated to operate the Instron test machine. As the test was performed (FIGS. 8A–8D), the tensile loads on the control line were recorded by the test machine throughout the complete removal of the control line from the device assembly. The data were expressed in graphic form as illustrated in FIGS. 9 and 10.

As seen in FIG. 9, the ePTFE control line experienced a series of oscillating forces as the control line was pulled upon and the first few slip knots, or chain stitches, in the series undone. As the control line was pulled further and the next few knots or stitches in the series removed from the confinement means, the amount of pulling force required to remove these knots or stitches decreased to nearly zero. Part of this reduction in pulling force is attributed to radial expansion of the emerging stent-graft against the confinement means. These expansion forces can be of sufficient magnitude to cause the knots or stitches to become undone from the confinement means without further pulling of the control line. This property of the ePTFE control line does not provide for tactile feedback of the release of individual knots or stitches following release of the few first knots or stitches.

FIG. 10 shows the control line of the present invention underwent a series of oscillating forces of greater magnitude than the ePTFE control line as the control line was pulled upon and the few first knots or stitches undone from the confinement means. Unlike the ePTFE control line, the control line of the present invention underwent a further series of oscillating forces as the control line was pulled and the remaining knots or stitches removed from the confinement means. The series of peaks shown in FIG. 10 provide a graphic representation of the tactile feedback experienced by a practitioner as the control line of the present invention is operated. The results shown in FIG. 10 also indicate the control line of the present invention has a greater resistance to unknotting or unstitching than the ePTFE control line.

Example 5

This example describes a test method and apparatus designed to demonstrate quantitative differences in the ability of different control lines to resistance pulling through a slip knot. As with the qualitative data of Example 4, the results of this "slip knot pull through test" can be extrapolated to provide an indication of how the different control lines will behave when the control line is chain stitched to a confinement means in a medical device assembly.

One control line used in this example was made of porous expanded polytetrafluoroethyene and is described in Example 4. The other control line is a preferred embodiment of a component of the present invention and is described in Example 1.

Figure 11:
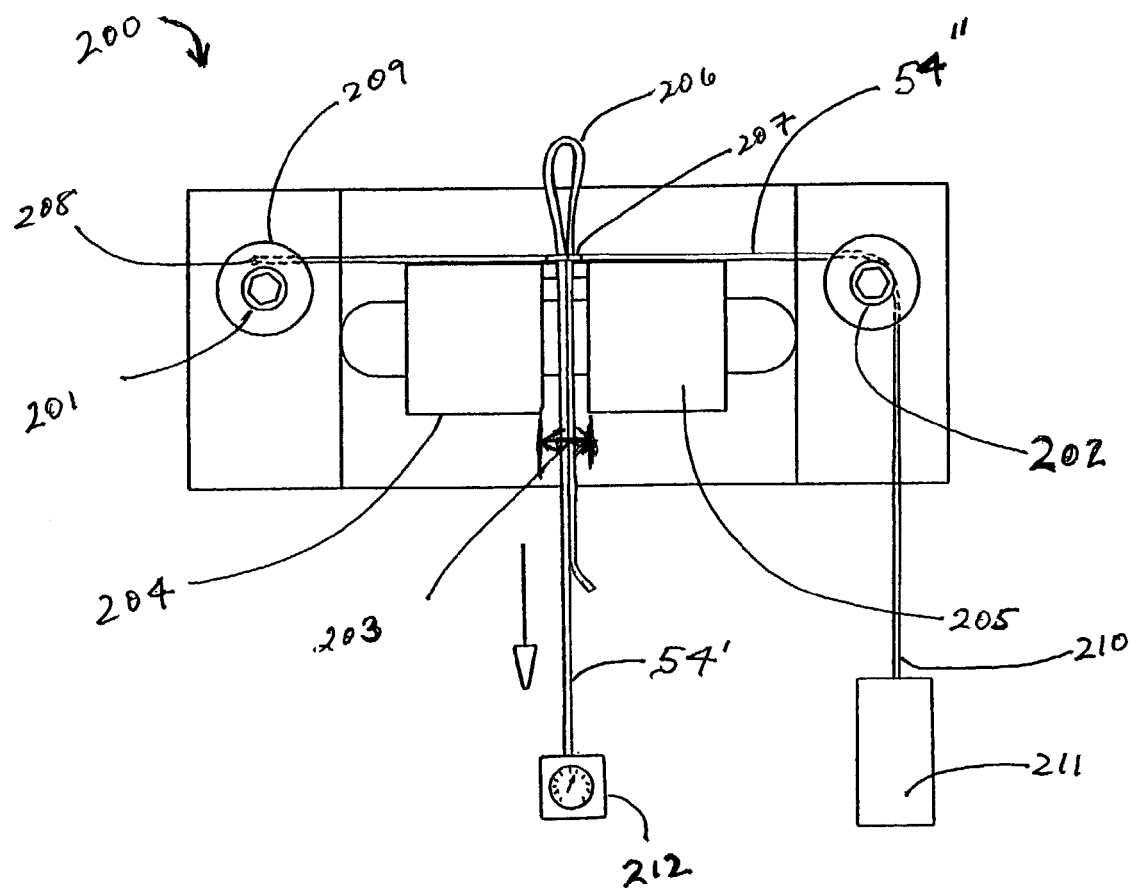
FIG. 11 illustrates a test apparatus described in Example 5.
Figure 11A:
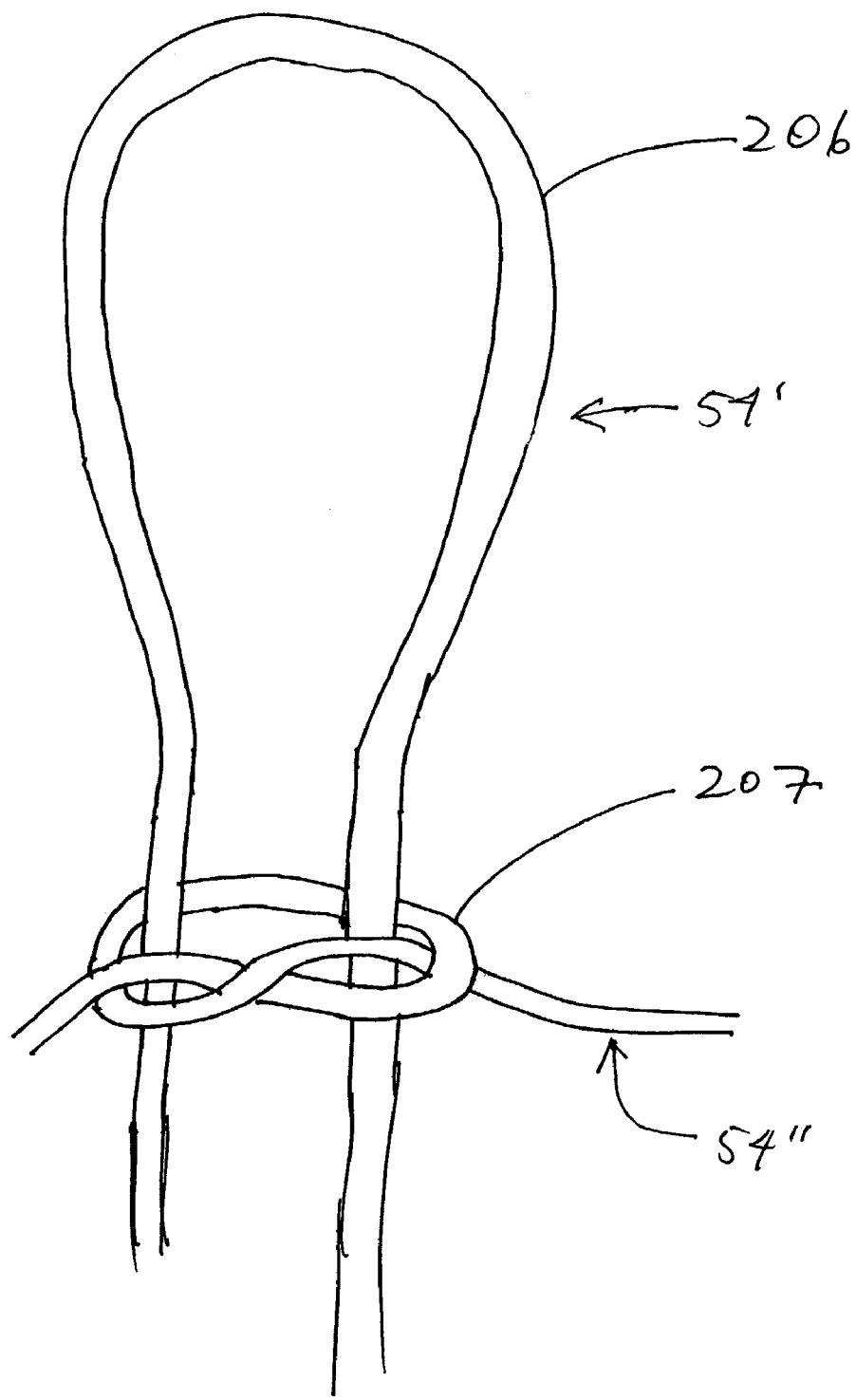
FIG. 11A illustrates a magnified view of the slip knot used in Example 5.

The slip knot pull through test of this example utilized an apparatus as illustrated in FIG. 11. The apparatus (200) had two posts (201, 202) for securing a second control line material (54"). The apparatus also had an adjustable gap (203) for supporting a knot tied around a first control line material (54') with the second control line material (54"), similar to the way a fabric supports a stitched thread. A gap (203) of known width was provided in the apparatus (200) by adjusting two moveable solids (204, 205) with the aid of a feeler gauge. In this test, the gap was set at approximately 0.5 mm (0.020 inches).

To perform the test for the ePTFE control line, first and second lengths of control line material (approximately 30–45 cm long (12–18 inches)) were obtained. Loops were formed on one end of each control line and secured with a bowline or equivalent slip-resistant knot. As shown in FIG. 11, the first of these control lines (54') was bent at its midpoint, without kinking, to form a 180-degree bend (206). The second control line (54") was then tied around the first control line (54') to capture the 180-degree bend (206) as shown in FIG. 11. The second control line (54") was secured around the first control line (54') with a single throw knot (207). The single throw knot (207) was placed approximately as shown in FIG. 11.

Once the second control line (54") was secured around the first control line (54'), the end of the second control line without a loop (208) was secured to one of the two posts (201) on the testing apparatus (200). This end of second control line (208) was secured to the post (201) by tightening a screw on the post to capture the control line between a washer (209) and the test apparatus body. The second control line (54") was then draped over the other post (202) on the test apparatus so as to allow the looped-end of the control line (210) to freely hang below the post (202). As the second control line (54") was properly positioned in the apparatus, the first control line (54') was also properly placed in the apparatus. The first control line (54') was placed in the gap (203) portion of the apparatus so both ends hung freely. The portions of the test apparatus that defined the gap (204, 205) were used to support the knot (207) surrounding the first control line (54').

When the first and second control lines (54', 54") were properly positioned in the test apparatus, a weight (211) of known value was hung from the loop of the second control line, placing the second control line under a known amount of tension. Weights representing approximately one eighth of the force to break of the particular control line material were used in the test. When the second control line (54") was fully supporting the known weight, the looped end of the second control line (210) was secured to the apparatus by tightening the screw and washer combination on the post (202) supporting the looped end of the control line (54"). Once tension was applied to the second control line, the positioning of the knot surrounding the first control line relative to the gap was confirmed and adjusted if necessary. By hanging a weight of known value on the loop of the second control line, a known and repeatable amount of force was used to tension the knot surrounding the first control line.

Once the control lines were properly positioned and tension set on the second control line, an Ametek AccuForce III® digital force gauge (Ametek, Mansfield & Green Division, Largo, Fla.), with a 0–4.5 kg (0–10 lb) range was zeroed and set to record a peak load. The hook on the Ametek force gauge (212) was used to engage the loop on the first control line (54'). The Ametek force gauge (212) was then gradually lowered so that the bend (206) of the first control line (54') was pulled through the knot (207) of the second control line (54"). The peak force registered on the Ametek force gauge was then recorded.

This test was repeated for the construct of Example 1.

The results for the construct described in Example 1 and the ePTFE control line material of Example 4 are shown in Table 1.

TABLE 1

Slip Knot Pull Through Test Results

| Control Line Material | Knot tension force (kg) | Pull Through Force (kg) |
| --- | --- | --- |
| Example 1 Control Line | 1 | 0.9 |
|  | 1 | 0.8 |
|  | 1 | 0.9 |
| ePTFE Control Line | 0.25 | 0.2 |
|  | 0.25 | 0.3 |
|  | 0.25 | 0.2 |

These results demonstrate that the control line as described in Example 1 produced higher pull through forces when tested using the method described in Example 5 as compared to a porous expanded polytetrafluoroethylene control line. The magnitude of the difference in Pull Through Force between the two control lines was expected to be less than the recorded values because of additional lubriciousness imparted to the polyaramid core material by the lubricious fluoropolymer covering applied to the polyaramid core.

In order to normalize for different control line diameters, a convenient way of expressing the pull through force in the slip knot pull through test is using the ratio resulting from dividing the pull through force for a control line (when tested using the method described in Example 5) by its diameter. Using the data of Table 1, these ratios were calculated for the inventive control line and a porous expanded polytetrafluoroethylene control line. The inventive control line had a diameter of approximately 0.3 mm (0.01 inches) and the porous expanded polytetrafluoroethylene control line had a diameter of approximately 0.3 mm (0.01 inches). The calculated ratios are shown in Table 2.

TABLE 2

Normalized Slip Knot Pull Through Test Results

| Control Line Material | Knot Tension Force (kg) | Pull Through Force (kg) | Pull Through Force (kg) Coupling Member Diameter (mm) |
|---|---|---|---|
| Example 1 Control Line | 1 | 0.9 | 3 |
|  | 1 | 0.8 | 2.7 |
|  | 1 | 0.9 | 3 |
| ePTFE Control Line | 0.25 | 0.2 | 0.7 |
|  | 0.25 | 0.3 | 1 |
|  | 0.25 | 0.2 | 0.7 |

Example 6

This example describes the construction of an implantable medical device assembly (140) using the control line of Example 1. The assembly included an expandable stent-graft (56) in a compacted or collapsed configuration enclosed by confinement means (52) used to maintain the stent-graft in a compacted configuration. The removable control line (54) was attached to the confinement means (52) and threaded through the delivery catheter (100) to a hub or control means (141) at the proximal end of the assembly. The hub (141) had a control knob (142') attached to a guidewire (142) running the length of the catheter (100) and through the lumen of the stent-graft (56). The hub (141) also had a control knob (144) attached to the control line.

Construction of the assembly (FIG. 6G, 140) began by obtaining an expandable stent-graft (56) from W.L. Gore & Associates, Inc., Flagstaff, Ariz. under the tradename EXCLUDER™ Bifurcated Endoprosthesis. A multilumen delivery catheter (100) was provided with a guidewire (142) placed inside the innermost lumen of the catheter. The guidewire (142) was threaded through the lumen of the stent-graft (56) and the stent-graft compacted, or collapsed, along its length over the guidewire (142). Barrier elements were placed on the guidewire at the proximal (67) and distal (68) ends of the stent-graft (56) to assist in confining the stent-graft. The proximal barrier element (67) had an aperture (69) through which the control line (54) was threaded from the confinement means (52) through the catheter to the knob (144) in the hub (141).

Confinement means (52) for containing the compacted stent-graft was fabricated in the form of a sleeve from a sheet of ePTFE and the control line of Example 1. To form the sleeve, an ePTFE reinforcing filament (53) was placed along each edge of the sheet. The ePTFE sheet was folded in half to bring the two reinforcing filaments together along a common edge. A seam was sewn along the common edge of the sheet, inside the reinforcing filament (53), with a length of the control line (54) of Example 1. The seam was formed with a chain-stitch pattern using a Custom Singer Sewing Machine, model number 24-7, available from Sew Fine, LLC, San Francisco, Calif. The stitch length was set at 10–14 stitches per inch. A top view of the chain-stitch pattern is illustrated in FIG. 4.

The chain-stitched seam was secured by forming a loop (54a) in the control line (54) near the distal end of the ePTFE sleeve and tying two slip knots (54b) at the base of the loop. The loop was further secured by tucking the loop under some of the chain-stitches as shown in FIG. 4. A temporary clip (not shown) was placed on the end of the loop to prevent the stitching from coming unstitched prematurely. The temporary clip is removed from the assembly before packaging.

The compacted stent-graft (56) was placed inside the sleeve (52) as shown in FIGS. 6A–6F. As seen in FIG. 6G, the remaining length of control line (54) was doubled back on itself along the length of the sleeve (52) and threaded through an aperture (69) in the proximal barrier element (67). The control line continued through the lumen of the catheter (100) to a control knob (144) attached to a hub (141) located at the proximal end of the catheter (FIG. 6G).

We claim:

1. An implantable medical device assembly comprising:
    an expandable endovascular device;
    confinement means containing said expandable endovascular device in a compacted configuration;
    at least one control line comprising a monofilamentous non-fluoropolymer core and an expanded polytetrafluoroethylene cover surrounding the core, wherein the control line is removably attached to the confinement means by stitching; and
    wherein the stitched control line has a stiffness sufficient to require essentially every stitch in the confinement means to be removed one stitch at a time;
    whereby the stitched control line provides tactile feedback to a practitioner as essentially every stitch is removed from said confinement means, and wherein the tactile feedback is in the form of oscillating pulling forces that vary in magnitude as substantially every stitch is removed from the confinement means.

2. The implantable medical device assembly of claim 1 wherein said control line has a ratio of ultimate tensile strength divided by slip knot pull through force of greater than about 4.

3. The implantable medical device assembly of claim 1 wherein said control line has a ratio of ultimate tensile strength divided by slip knot pull through force of greater than about 5.

4. The implantable medical device assembly of claim 1 wherein said control line has a ratio of ultimate tensile strength divided by slip knot pull through force of greater than about 6.

5. The implantable medical device assembly of claim 1 wherein the endovascular device is a stent.

6. The implantable medical device assembly of claim 5 wherein the stent has a permanent covering placed on at least a portion of the stent.

7. The implantable medical device assembly of claim 1 wherein the endovascular device is a stent-graft.

8. The implantable medical device assembly of claim 1 wherein the endovascular device is an intra-cardiac device.

9. The implantable medical device assembly of claim 1 wherein the control line has a tensile strength of at least 14 pounds force.

10. The implantable medical device assembly of claim 1 wherein the core comprises an aramid polymer.

11. The implantable medical device assembly of claim 1 wherein the core comprises a liquid crystal polymer.

12. The implantable medical device assembly of claim 1 wherein the core comprises polyethyleneterephthalate.

13. The implantable medical device assembly of claim 1 wherein the core comprises polyamid.

* * * * *